United States Patent
Jung et al.

(10) Patent No.: US 7,150,961 B2
(45) Date of Patent: Dec. 19, 2006

(54) ADDITIVE FOR PHOTORESIST COMPOSITION FOR RESIST FLOW PROCESS

(75) Inventors: Min Ho Jung, Kyoungki-do (KR);
Sung Eun Hong, Kyoungki-do (KR);
Jae Chang Jung, Kyoungki-do (KR);
Geun Su Lee, Kyoungki-do (KR); Ki Ho Baik, Kyoungki-do (KR)

(73) Assignee: Hynix Semiconductor Inc., Kyungki-do (KR)

( * ) Notice: Subject to any disclaimer, the term of this patent is extended or adjusted under 35 U.S.C. 154(b) by 0 days.

(21) Appl. No.: 10/789,055

(22) Filed: Feb. 27, 2004

(65) Prior Publication Data

US 2004/0166437 A1 Aug. 26, 2004

Related U.S. Application Data

(62) Division of application No. 09/878,803, filed on Jun. 11, 2001, now Pat. No. 6,770,414.

(30) Foreign Application Priority Data

Jun. 15, 2000 (KR) ............... 2000-32984

(51) Int. Cl.
- *G03F 7/039* (2006.01)
- *G03F 7/20* (2006.01)
- *G03F 7/30* (2006.01)
- *G03F 7/40* (2006.01)

(52) U.S. Cl. ............ 430/326; 430/325; 430/330; 430/311; 430/905; 430/914; 430/270.1

(58) Field of Classification Search ............ 430/325, 430/326, 330, 311, 905, 914
See application file for complete search history.

(56) References Cited

U.S. PATENT DOCUMENTS

| | | | |
|---|---|---|---|
| 5,276,126 A | 1/1994 | Rogler | 528/155 |
| 5,580,694 A | 12/1996 | Allen et al. | 430/270.1 |
| 5,786,131 A | 7/1998 | Allen et al. | 430/325 |
| 5,998,099 A | 12/1999 | Houlihan et al. | 430/311 |
| 6,180,316 B1 | 1/2001 | Kajita et al. | 430/270.1 |
| 6,268,106 B1 | 7/2001 | Park et al. | 430/270.1 |
| 6,391,518 B1 | 5/2002 | Jung et al. | 430/270.1 |
| 6,497,987 B1 | 12/2002 | Kim et al. | 430/270.1 |

FOREIGN PATENT DOCUMENTS

JP 11-109628 4/1999

OTHER PUBLICATIONS

*Korean Intellectual Property Office Notice of Rejection*, corresponding to co-pending Korean Patent Application Serial No. 10-2000-0032984, Korean Intellectual Property Office, dated Dec. 27, 2005, 5 pages.

*Primary Examiner*—Sin Lee
(74) *Attorney, Agent, or Firm*—Marshall, Gerstein & Borun LLP

(57) ABSTRACT

The present invention provides an additive for a photoresist composition for a resist flow process. A compound of following Formula 1 having low glass transition temperature is added to a photoresist composition containing a polymer which is not suitable for the resist flow process due to its high glass transition temperature, thus improving a flow property of the photoresist composition. As a result, the photoresist composition comprising an additive of Formula 1 can be used for the resist flow process.

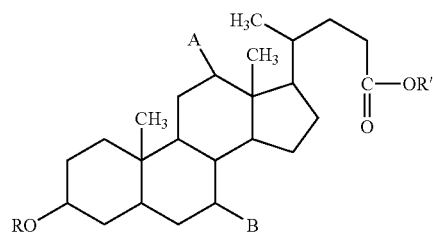

Formula 1 wherein, A, B, R and R' are as defined in the specification of the invention.

18 Claims, 2 Drawing Sheets

ADDITIVE FOR PHOTORESIST COMPOSITION FOR RESIST FLOW PROCESS

This is a divisional of U.S. application Ser. No. 09/878,803 filed Jun. 11, 2001 now U.S. Pat. No 6,770,414.

BACKGROUND OF THE INVENTION

1. Field of the Invention

The present invention relates to an additive for a photoresist composition for a resist flow process, and a photoresist composition comprising the same. In particular, the present invention relates to a photoresist composition comprising an additive which lowers the glass transition temperature of the photoresist polymer, and a method for forming a contact hole using the same.

2. Description of the Background Art

Recently, semiconductor devices have been highly integrated. It is difficult to form a contact hole having a high resolution in lithography process. Currently, a contact hole patterning limit of KrF lithography is about 0.18 μm. Resist flow is a processing technology for forming a fine contact hole which exceeds the resolution of the exposing device.

The resist flow process has recently made remarkable developments and so that it is now used in mass production processes. The technology generally involves an exposure process and a development process. This process forms a photoresist contact hole having a resolution equal to that of the exposing device. The process also includes heating the photoresist to a temperature higher than the glass transition temperature of the photoresist which causes the photoresist to flow. The contact hole gets smaller by the flow of photoresist until a fine contact hole necessary for the integration process is obtained.

Most of the KrF resists can be flow processed, though having different profiles after the flow process. That is, the KrF resist mainly containing polyvinylphenol consists of a structure having appropriate $T_g$ for the flow. However, a resist used for ArF lithography has so high $T_g$ that it cannot be flow processed. Especially, cycloolefine resists have a $T_g$ over about 200° C., and thus is not suitable for the resist flow process. An appropriate temperature for the resist flow process ranges between the $T_g$ of the photoresist polymer and a decomposition temperature $(T_d)$ where the polymer starts to be decomposed. Therefore, the polymer having high $T_g$ cannot be used for a resist flow because the $T_g$ and $T_d$ have only a slight difference. Therefore, there is a need for a modified resist material with a suitable disparity between the $T_g$ and $T_d$ thereby making it suitable for resist flow processing.

SUMMARY OF THE DISCLOSURE

An additive for a photoresist composition thereby making it suitable for a resist flow process is disclosed.

Photoresist compositions comprising such additive for a resist flow process are also disclosed.

A resist flow process for forming a photoresist pattern using such photoresist composition is also disclosed.

A contact hole formation method employing the photoresist pattern formed by the above-described process is also disclosed.

DETAILED DESCRIPTION OF THE PREFERRED EMBODIMENTS

Figure 1:
FIG. 1 shows a first photoresist pattern obtained in Example 11.

The present invention provides an additive for a photoresist composition for a resist flow process, and a photoresist composition comprising the same. In particular, the present invention provides a photoresist composition comprising the additive which lowers the glass transition temperature of the photoresist polymer, thereby improving a flow property of photoresist composition during a resist flow process.

In one particular aspect, the present invention provides an additive of following Formula 1 for the photoresist composition which is used for a resist flow process:

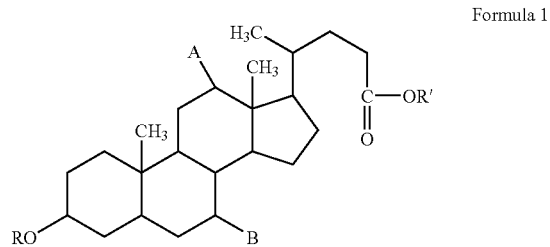

Formula 1 wherein, A is H or —OR",

B is H or —OR''', and

R, R', R" and R''', are independently substituted or unsubstituted linear or branched $C_1$–$C_{10}$ alkyl, substituted or unsubstituted linear or branched $C_1$–$C_{10}$ alkoxyalkyl, substituted or unsubstituted linear or branched $C_1$–$C_{10}$ alkylcarbonyl, or substituted or unsubstituted linear or branched $C_1$–$C_{10}$ alkyl containing at least one hydroxyl group (—OH).

Exemplary additives of Formula 1 include, but are not limited to, the following compounds of Formulas 2 to 7:

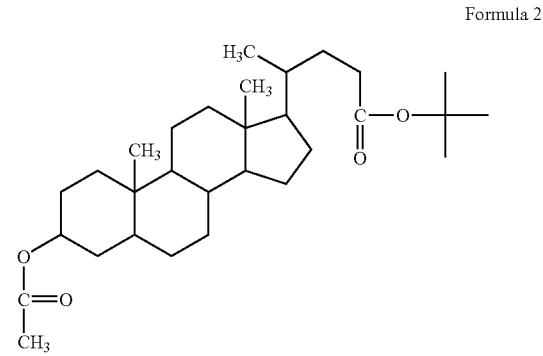

Formula 2

Formula 3
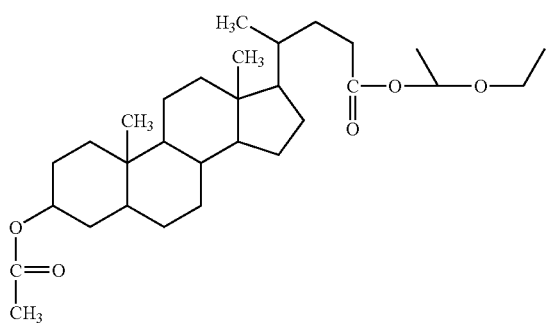

Formula 4
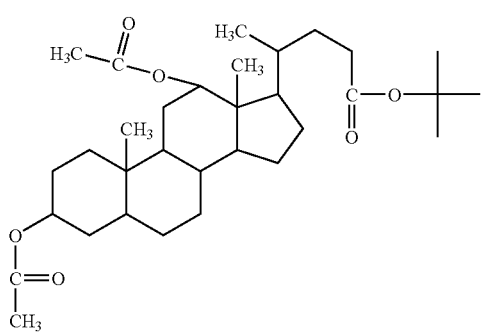

Formula 5
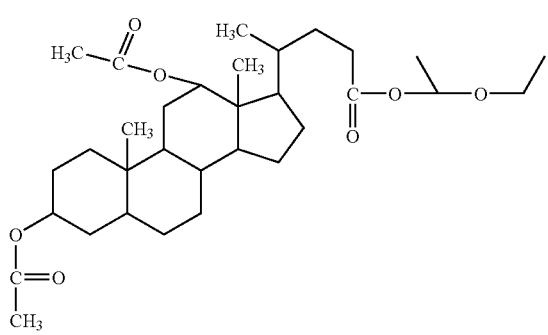

Formula 6
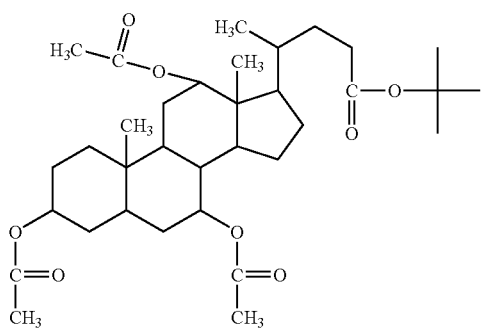

Formula 7
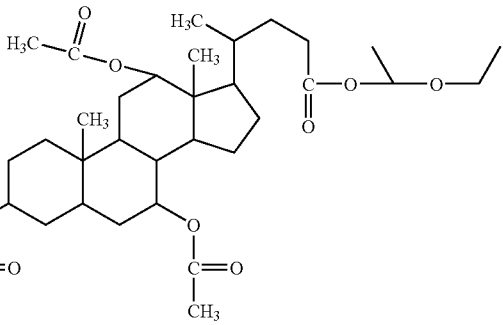

Another aspect of the present invention provides a photoresist composition comprising a photoresist polymer, a photoacid generator, an organic solvent and the additive of Formula 1.

The present photoresist composition comprising the additive of Formula 1 is suitable for the resist flow process. As described above, a photoresist polymer having very high glass transition temperature ($T_g$) cannot be used for resist flow process since the $T_g$ and decomposition temperature ($T_d$) have only a slight difference. However, the additive of Formula 1 serves to lower the $T_g$, thus improving a flow property of the photoresist composition. As a result, the photoresist composition can be suitably employed for the resist flow process.

The photoresist polymer of the photoresist composition can be any currently known chemically amplified photoresist polymer disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0789 278 (Aug. 13, 1997) and U.S. Pat. No. 6,132,926 (Oct. 17, 2000). It is preferable that the PR polymer be prepared by radical additional polymerization of cycloolefin comonomers and the ring structures of the cycloolefin comonomers remains in the main chain of the PR polymer. An exemplary photoresist polymer employed in the photoresist composition includes a compound of following Formulas 8 or 9:

Formula 8
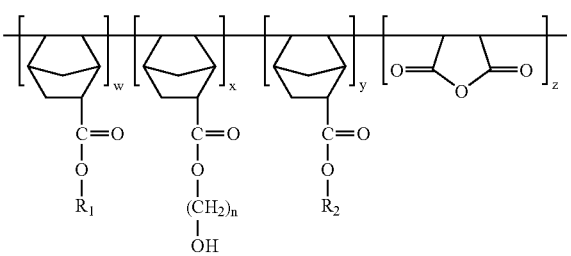

Formula 9

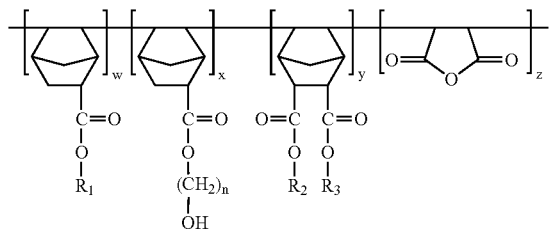

wherein, R₁ is an acid labile protecting group;
R₂ is hydrogen;
R₃ is hydrogen, substituted or unsubstituted linear or branched $C_1$–$C_{10}$ alkyl, substituted or unsubstituted linear or branched $C_1$–$C_{10}$ alkoxyalkyl, or substituted or unsubstituted linear or branched $C_1$–$C_{10}$ alkyl containing at least one hydroxyl -group (—OH);
n is an integer from 1 to 5; and
w, x, y and z individually denote the mole ratio of each monomer, preferably with proviso that w+x+y=50 mol %, and z is 50 mol %.

The acid labile protecting group can be any of the known protective groups that can be substituted by an acid and functions to prevent the compound to which the group is bound from dissolving in the alkaline developer solution. Conventional acid labile protecting groups are disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0789 278 (Aug. 13, 1997) and U.S. Pat. No. 6,132,926 (Oct. 17, 2000). Preferable acid labile protecting groups are selected from the group consisting of tert-butyl, tetrahydropyran-2-yl, 2-methyl tetrahydropyran-2-yl, tetrahydrofuran-2-yl, 2-methyl tetrahydrofuran-2-yl, 1-methoxypropyl, 1-methoxy-1-methylethyl, 1-ethoxypropyl, 1-ethoxy-1-methylethyl, 1-methoxyethyl, 1-ethoxyethyl, tert-butoxyethyl, 1-isobutoxyethyl and 2-acetylmenth-1-yl.

Preferably, the photoresist polymer of Formulas 8 or 9 include, but are not limited to, compounds of Formulas 10 to 13:

Formula 10

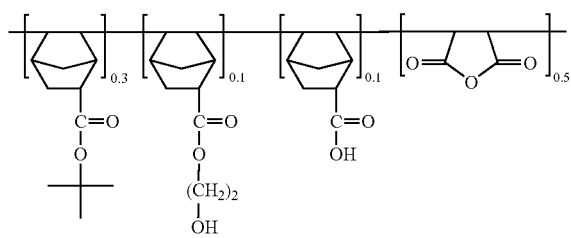

Formula 11

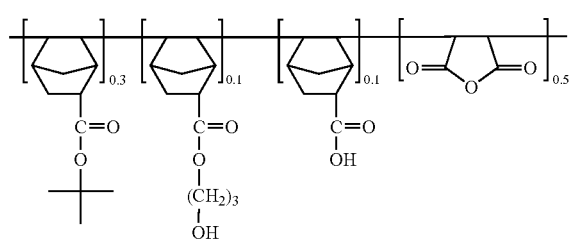

Formula 12

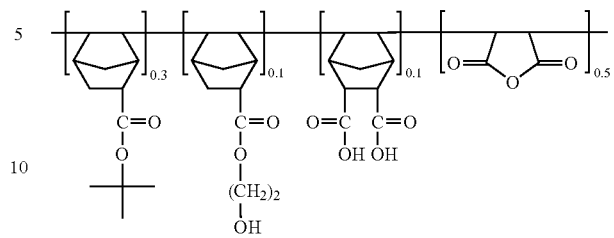

Formula 13

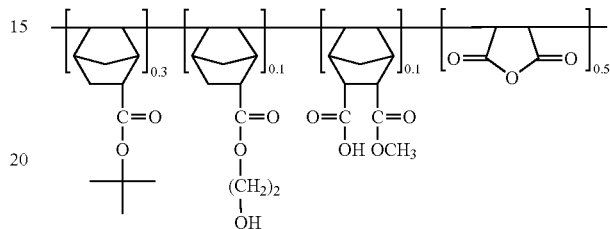

The additive of Formula 1 is used in an amount of 1 to 70% by weight of the photoresist polymer employed.

Any of known photoacid generator, which is able to generate acids by light, can be used in photoresist composition of the present invention. Conventional photoacid generators are disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0789 278 (Aug. 13, 1997) and U.S. Pat. No. 6,132,926 (Oct. 17, 2000).

Preferred photoacid generators include sulfides or onium type compounds. In one particular embodiment of the present invention, the photoresist generator is at least one compound selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluororphosphate, triphenylsulfonium hexafluoroarsenate, triphenylsulfonium hexafluoroantimonate, triphenylsulfonium triflate and dibutylnaphthylsulfonium triflate. The photoacid generator is used in an amount ranging from about 0.01 to about 10% by weight of the photoresist polymer employed.

While a variety of organic solvents, disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0789 278 (Aug. 13, 1997) and U.S. Pat. No. 6,132,926 (Oct. 17, 2000), are suitable for use in the photoresist composition of the present invention, the organic solvent selected from the group consisting of propyleneglycol methyl ether acetate, ethyl lactate, methyl 3-methoxypropionate, ethyl-3-ethoxypropionate and cyclohexanone is preferred. The amount of solvent used is preferably in the range of from about 100% to 1000% by weight of the photoresist polymer.

A process is also disclosed for forming a photoresist pattern, by introducing the resist flow process and using the photoresist composition containing the additive of Formula 1.

The process for forming the photoresist pattern comprises the steps of:

(a) coating the above described photoresist composition containing the additive of Formula 1 on a substrate to form a photoresist film;

(b) forming a first photoresist pattern using a lithography process (preferably the first photoresist pattern has a lower resolution than the maximum resolution of an exposing device); and (c) producing a second photoresist pattern from the first photoresist pattern using a resist flow (i.e., flow bake) process.

Preferably, the second photoresist pattern has a higher resolution than the first photoresist pattern. More preferably, the second photoresist pattern,has a higher resolution than the maximum resolution of the exposing device of the step (b).

The temperature of the resist flow process of step (c) is preferably in the range of from about 120 to about 190° C.

A method is also disclosed for preparing a contact hole using the photoresist composition described above. In particular, a substrate coated with the photoresist composition of the present invention is etched using the second photoresist pattern (as described above) as an etching mask to form the contact hole.

Yet another embodiment provides a semiconductor element that is manufactured using the photoresist composition described above.

The present invention will now be described in more detail by referring to the examples below, which are not intended to be limiting.

I. Synthesis of Additive

EXAMPLE 1

Synthesis of Compound of Formula 2

To tetrahydrofuran was added 0.1 mole of lithocholic acid and 0.1 mole of triethylamine, and the resulting solution was maintained at a temperature below 4° C. in an ice bath. 0.12 mole of acetyl chloride was slowly added thereto, and the resulting solution was reacted for 8 hours. Thereafter, residual solvent was removed by using a vacuum distillator. A compound was extracted by using ethyl acetate, and washed with water a few times, to obtain 3α-acetylcholanic acid. To tetrahydrofuran was added 0.2 mole of 3α-acetylcholanic acid thus obtained and 0.3 mole of acetic anhydride. 0.21 mole of tert-butanol was added to the resulting solution. Then, the resulting solution was reacted for 12 hours, to obtain 3α-acetyl tert-butyl lithocholate of formula 2 (yield: 68%).

EXAMPLE 2

Synthesis of Compound of Formula 3

To tetrahydrofuran was added 0.1 mole of lithocholic acid and 0.1 mole of triethylamine, and the resulting solution was maintained at a temperature below 4° C. in an ice bath. 0.12 mole of acetyl chloride was slowly added thereto, and the resulting solution was reacted for 8 hours. Thereafter, residual solvent was removed by using a vacuum distillator. A compound was extracted by using ethyl acetate, and washed with water a few times, to obtain 3α-acetylcholanic acid. To tetrahydrofuran was added 0.2 mole of 3α-acetyl cholanic acid thus obtained and a slight amount of p-toluensulfonic acid. 0.21 mole of ethylvinylether was added to the resulting solution. Then, the resulting solution was reacted for 12 hours, to obtain 3α-acetylethoxyethyl lithocholate of formula 3 (yield: 70%).

EXAMPLE 3

Synthesis of Compound of Formula 4

To tetrahydrofuran was added 0.1 mole of lithocholic acid and 0.1 mole of triethylamine, and the resulting solution was maintained at a temperature below 4° C. in an ice bath. 0.24 mole of acetyl chloride was slowly added thereto, and the resulting solution was reacted for 8 hours. Thereafter, residual solvent was removed by using a vacuum distillator. A compound was extracted by using ethyl acetate, and washed with water a few times, to obtain 3α,10α-diacetylcholanic acid. To tetrahydrofuran was added 0.2 mole of 3α,10α-diacetylcholanic acid thus obtained and 0.3 mole of acetic anhydride. 0.21 mole of tert-butanol was added to the resulting solution. Then, the resulting solution was reacted for 12 hours, to obtain 3α,10α-diacetyl tert-butyl lithocholate of formula 4 (yield: 69%).

EXAMPLE 4

Synthesis of Compound of Formula 5

The procedure of Example 2 was repeated but using 3α,10α-diacetylcholanic acid obtained in Example 3, instead of 3α-acetylcholanic acid, to obtain 3α,10α-diacetylethoxyethyl lithocholate of formula 5 (yield: 72%).

EXAMPLE 5

Synthesis of Compound of Formula 6

To tetrahydrofuran was added 0.1 mole of lithocholic acid and 0.1 mole of triethylamine, and the resulting solution was maintained at a temperature below 4° C. in an ice bath. 0.36 mole of acetyl chloride was slowly added thereto, and the resulting solution was reacted for 8 hours. Thereafter, residual solvent was removed by using a vacuum distillator. A compound was extracted by using ethyl acetate, and washed with water a few times, to obtain 3α,5α,10α-triacetylcholanic acid. To tetrahydrofuran was added 0.2 mole of 3α,5α,10α-triacetylcholanic acid thus obtained and 0.3 mole of acetic anhydride. 0.21 mole of tert-butanol was added to the resulting solution. Then, the resulting solution was reacted for 12 hours, to obtain 3α,5α,10α-triacetyl tert-butyl lithocholate of formula 6 (yield: 70%).

EXAMPLE 6

Synthesis of Compound of Formula 7

The procedure of Example 2 was repeated but using 3α,5α,10α-triacetylcholanic acid obtained in Example 5, instead of 3α-acetylcholanic acid, to obtain 3α,5α,10α-triacetylethoxyethyl lithocholate of Formula 7 (yield: 71%).

II. Synthesis of Photoresist Polymer

PREPARATION EXAMPLE 1

Synthesis of Poly(tert-butyl 5-norbornene-2-carboxylate/2-hydroxyethyl 5-norbornene-2-carboxylate/5-norbornene-2-carboxylic acid/maleic anhydride)

To tetrahydrofuran or toluene was added 0.5 to 0.95 mole of tert-butyl 5-norbornene-2-carboxylate, 0.05 to 0.8 mole of 2-hydroxyethyl 5-norbornene-2-carboxylate, 0.01 to 0.2 mole of 5-norbornene-2-carboxylic acid, 0.5 to 1 mole of maleic anhydride and 0.5 to 10 g of 2,2'-azobisisobutyronitrile (AIBN).

The mixture was stirred at 60 to 70° C. for 4 to 24 hours under an nitrogen or argon atmosphere. The resulting polymer was precipitated in ethyl ether or hexane, and dried to obtain the title polymer of Formula 10.

PREPARATION EXAMPLE 2

Synthesis of Poly(tert-butyl 5-norbornene-2-carboxylate/3-hydroxypropyl 5-norbornene-2-carboxylate/5-norbornene-2-carboxylic acid/maleic anhydride)

The procedure of Preparation Example 1 was repeated but using 3-hydroxypropyl 5-norbornene-2-carboxylate, instead of 2-hydroxyethyl 5-norbornene-2-carboxylate, to obtain the title polymer of Formula 11.

PREPARATION EXAMPLE 3

Synthesis of Poly(tert-butyl 5-norbornene-2-carboxylate/2-hydroxyethyl 5-norbornene-2-carboxylate/5-norbornene-2,3-dicarboxylic acid/maleic anhydride)

The procedure of Preparation Example 1 was repeated but using 5-norbornene-2,3-dicarboxylic acid, instead of 5-norbornene-2-carboxylic acid, to obtain the title polymer of Formula 12.

III. Preparation of Photoresist Composition

EXAMPLE 7

To propyleneglycol methyl ether acetate (100 g) was added the polymer of formula 10 (10 g), the compound of formula 2 (0.2 g), and triphenylsulfonium triflate (0.1 g). The mixture was then stirred and filtered through a 0.20 μm filter to obtain a photoresist composition.

EXAMPLE 8

To propyleneglycol methyl ether acetate (100 g) was added the polymer of formula 11 (10 g), the compound of formula 3 (0.2 g), and triphenylsulfonium triflate (0.1 g). The mixture was then stirred and filtered through a 0.20 μm filter to obtain a photoresist composition.

EXAMPLE 9

To propyleneglycol methyl ether acetate (100 g) was added the polymer of formula 12 (10 g), the compound of formula 4 (0.2 g), and triphenylsulfonium triflate (0.1 g). The mixture was then stirred and filtered through a 0.20 μm filter to obtain a photoresist composition.

EXAMPLE 10

To propyleneglycol methyl ether acetate (100 g) was added the polymer of formula 13 (10 g), the compound of formula 7 (0.2 g), and triphenylsulfonium triflate (0.1 g). The mixture was then stirred and filtered through a 0.20 μm filter to obtain a photoresist composition.

IV. Formation of Photoresist Pattern

EXAMPLE 11

Figure 2:
FIG. 2 shows a second photoresist pattern obtained in Example 11.

The photoresist composition prepared in Example 7 was coated on a wafer, baked at 100° C. for 90 seconds and exposed to light using a 0.60NA KrF exposing device (Nikon S201). The photoresist composition was post-baked at 130° C. for 90 seconds and developed in 2.38 wt % aqueous TMAH solution to obtain a 200 nm L/S pattern (see FIG. 1). The resulting pattern was flow baked at 153° C. for 90 seconds to obtain a 150 nm L/S pattern (see FIG. 2).

EXAMPLE 12

The procedure of Example 11 was repeated but using the photoresist composition prepared in Example 8, to obtain a 130 nm L/S pattern.

EXAMPLE 13

The procedure of Example 11 was repeated but using the photoresist composition prepared in Example 9, to obtain a 100 nm L/S pattern.

EXAMPLE 14

The procedure of Example 11 was repeated but using the photoresist composition prepared in Example 10, to obtain a 150 nm L/S pattern.

As discussed earlier, the additive of the present invention improves the flow property of the photoresist polymer for ArF which is not suitable for the resist flow process due to its high glass transition temperature, thus enabling the photoresist composition to be easily thermally flown. That is, the photoresist composition containing the additive can be suitably employed for the resist flow process for forming the contact hole.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A resist flow process for forming a photoresist pattern comprising the steps of:

(a) forming a first photoresist pattern on a substrate using a photoresist composition comprising a photoresist polymer, a photo acid generator, an organic solvent, and an additive selected from the group consisting of compounds of the following Formulas 3 to 7:

Formula 3

Formula 4

Formula 5

Formula 6

Formula 7 wherein said photoresist polymer is a compound selected from the group consisting of the following Formulas 8 and 9:

Formula 8

Formula 9 wherein, $R_1$ is an acid labile protecting group:
$R_2$ is hydrogen; $R_3$ is selected from the group consisting of hydrogen, $C_1$–$C_{10}$ alkyl, $C_1$–$C_{10}$ alkoxyalkyl, and $C_1$–$C_{10}$ alkyl containing at least one hydroxyl group (—OH);
n is an integer from 1 to 5; and w+x+y=50 mol %, and z is 50 mol %; and
(b) performing resist flow process onto the first photoresist pattern to obtain a second photoresist pattern.

2. The resist flow process according to claim 1, wherein said step (a) further comprises the steps of:
  (i) coating said photoresist composition on said substrate to form a photoresist film, wherein said substrate is a semiconductor devise; and
  (ii) producing said first photoresist pattern using a lithography process.

3. The resist flow process according to claim 1, wherein said first and second photoresist pattern comprises a contact hole pattern.

4. The resist flow process according to claim 1, wherein said resist flow process comprises heating to a temperature between Tg of photoresist polymer and a decomposition temperature ($T_d$) where the polymer starts to be decomposed.

5. The resist flow process according to claim 1, wherein said additive is present in an amount ranging from 1 wt % to 70 wt % of the photoresist polymer.

6. The resist flow process according to claim 1, wherein said photoacid generator is selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl inflate, triphenylsulfonium, hoxafluororphosphate, triphenylsulfonium hexafluoroarsenate, triphenylsulfonium hexafluoroantimonate, triphenylsulfonium triflate, dibutylnaphthylsulfonium triflate, and mixtures thereof.

7. The resist flow process according to claim 1, wherein said photoacid generator is present in an amount ranging from 0.01 wt % to 10 wt % of the photoresist polymer.

8. The resist flow process according to claim 1, wherein said organic solvent is selected from the group consisting of propyleneglycol methyl ether acetate, ethyl lactate, methyl 3-methoxypropionate, ethyl 3-ethoxypropionate and cyclohexanone.

9. The resist flow process according to claim 1, wherein said organic solvent is present in an amount ranging from 100 wt % to 1000 wt % of the photoresist polymer.

10. A resist flow process for forming a photoresist pattern comprising the steps of:
(a) forming a first photoresist pattern on a substrate using a photoresist composition comprising a photoresist polymer, a photo acid generator, an organic solvent, and an additive selected from the group consisting of compounds of following Formulas 3 to 7:

Formula 3

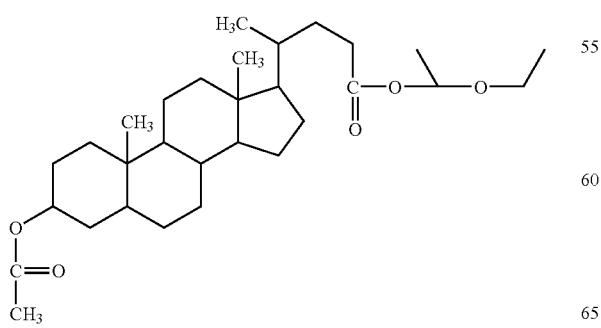

-continued

Formula 4

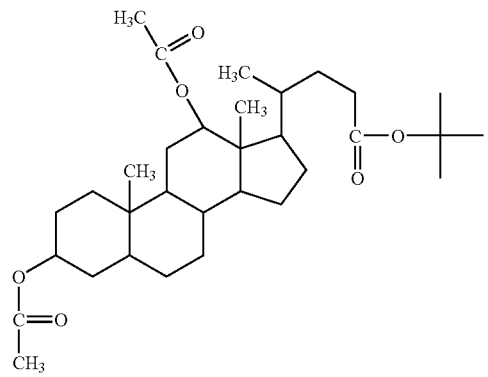

Formula 5

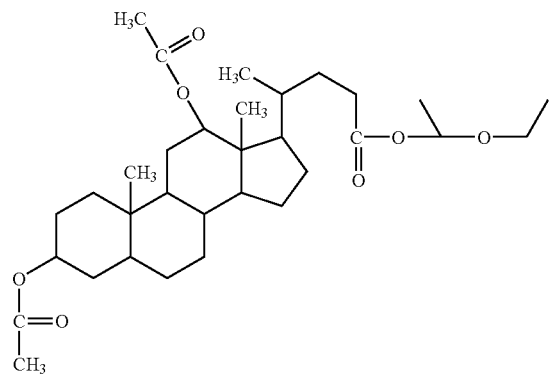

Formula 6

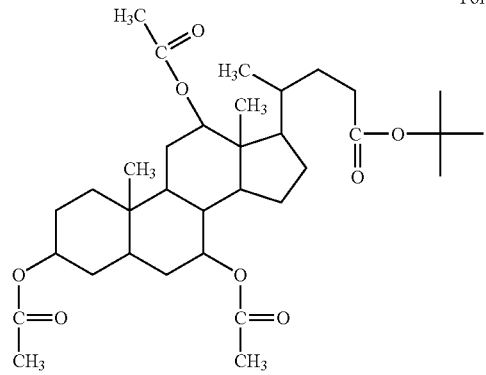

Formula 7

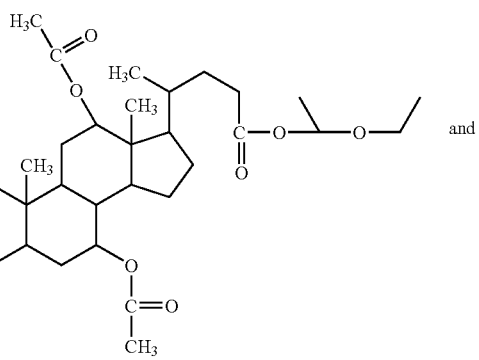

and (d) performing a resist flow process onto the first photoresist pattern to obtain a second photoresist pattern, wherein said photoresist polymer is selected from the group consisting of the following Formula 10 to 13:

Formula 10
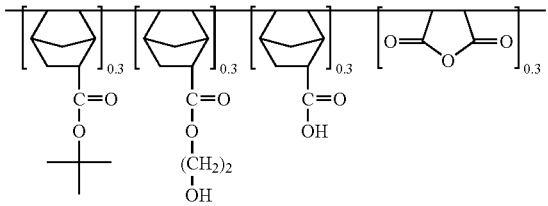

Formula 11
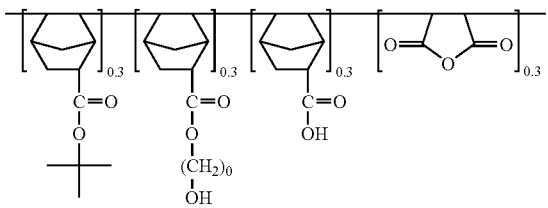

Formula 12
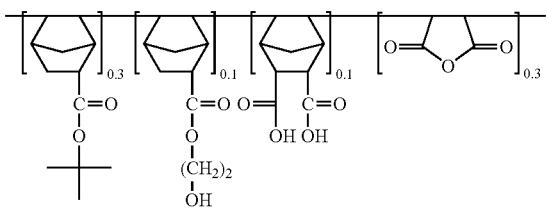

Formula 13
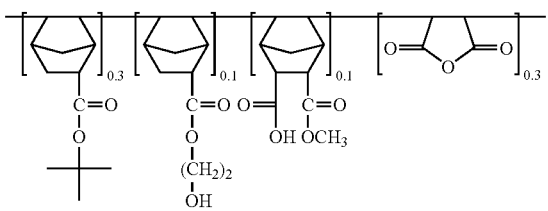

11. The resist flaw process according to claim 10, wherein step (a) further comprises the steps of:
  (i) coating said photoresist composition on said substrate to form a photoresist film, wherein said substrate is a semiconductor device; and
  (ii) producing said first photoresist pattern using a lithography process.

12. The resist flow process according to claim 10, wherein said first and second photoresist pattern comprises a contact hole pattern.

13. The resist flow process according to claim 10, wherein said resist flow process comprises heating to a temperature between Tg of the photoresist polymer and a decomposition temperature ($T_d$) where the polymer starts to be decomposed.

14. The resist flow process according to claim 10, wherein said additive is present in an amount ranging from 1 wt % to 70 wt % of the photoresist polymer.

15. The resist flow process according to claim 10, wherein said photoacid generator is selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluororphosphate, triphenylsulfonium hexafluoroarsenate, triphenylsulfonium hexafluoroantimonate, triphenylsulfonium triflate, dibutylnaphthylsulfonium triflate, and mixtures thereof.

16. The resist flow process according to claim 10, wherein amid photoacid generator is present in an amount ranging from 0.01 wt % to 10 wt % of the photoresist polymer.

17. The resist flow process according to claim 10, wherein said organic solvent is selected from the group consisting of propyleneglycol methyl ether acetate, ethyl lactate, methyl 3-methoxypropionate, ethyl 3-ethoxypropionate and cyclohexanone.

18. The resist flow process according to claim 10, wherein said organic solvent is present in an amount ranging from 100 wt % to 1000 wt % of the photoresist polymer.

* * * * *